US00PP29918P2

(12) United States Plant Patent
Hansen

(10) Patent No.: US PP29,918 P2
(45) Date of Patent: Nov. 27, 2018

(54) ***MANFREDA* PLANT NAMED 'CHERRY CHOCOLATE CHIP'**

(50) Latin Name: ***Manfreda undulata* (Klotzsch) Rose**
Varietal Denomination: Cherry Chocolate Chip

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/732,196

(22) Filed: Oct. 2, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and unique *Manfreda* plant named 'Cherry Chocolate Chip' characterized by flattened mound plant habit and variegated leaves having white margins and chartreuse centers with irregular greyed-purple spotting in the center and cherry red spotting on the margin. 'Cherry Chocolate Chip' readily produces tall, upright flower spikes of chocolate-mahogany-colored flowers. The new plant is suitable for the landscape garden or potted for indoor, garden or patio beautification.

2 Drawing Sheets

Botanical classification: *Manfreda undulata* (Klotzsch) Rose.

Variety denomination: 'Cherry Chocolate Chip'.

BACKGROUND OF THE INVENTION

The present invention relates to the new and distinct *Manfreda* plant, *Manfreda* 'Cherry Chocolate Chip' discovered by the inventor at a wholesale perennial nursery in Zeeland, Mich., USA as an uninduced whole-plant mutation in a tissue cultured crop of *Manfreda* 'Chocolate Chip' (not patented) on Aug. 10, 2012. The new plant has been successfully asexually propagated initially by division at the same nursery in Zeeland, Mich. and also by shoot tip tissue culture. Both methods of asexual propagation systems have been found to produce stable and identical plants that maintain all the unique characteristics of the original plant.

BRIEF SUMMARY OF THE INVENTION

*Manfreda* 'Chocolate Cherry Chip' differs from its parent, 'Chocolate Chip', as well as all other *Manfreda* cultivars known to the applicant. The most similar known variety is *Manfreda* 'Mint Chocolate Chip' (U.S. Plant Pat. No. 29,343). 'Mint Chocolate Chip' develops silvery-blue-green foliage with greyed-purple spotting compared to the white margined leaves with cherry-red spotting with chartreuse centers with greyed-purple spotting. The foliage of 'Mint Chocolate Chip' are thicker top to bottom than the new plant. The foliage of 'Cherry Chocolate Chip' is also narrower than 'Mint Chocolate Chip'. Compared with 'Chocolate Chip', the new plant has foliage with white margins that shows the greyed-purple spotting as a brighter cherry-red without the chartreuse chlorophyll in the margin.

*Manfreda* 'Cherry Chocolate Chip' differs from all other *Manfreda* known to the applicant, by the combination of the following traits:

1. Long, horizontal to arching, chartreuse, sinuate foliage with white margins;
2. Leaves develop irregular greyed-purple spotting that exhibits a cherry-red in regions of the white margin;
3. Moderate to rapid growth rate with good natural pup production;
4. Chocolate-mahogany flowers with long filaments and style on tall, stiff, vertical scapes.

BRIEF DESCRIPTION OF THE DRAWINGS

The photographs of the new plant demonstrates the overall appearance of the new plant including the unique traits as a two-year old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
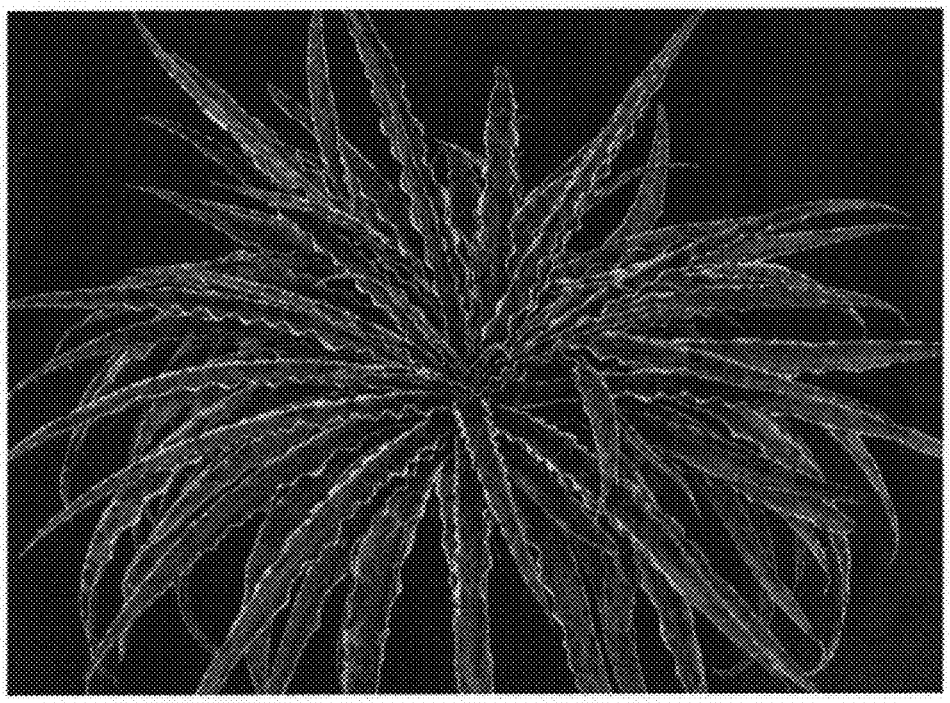
FIG. 1 shows the habit of the plant.
Figure 2:
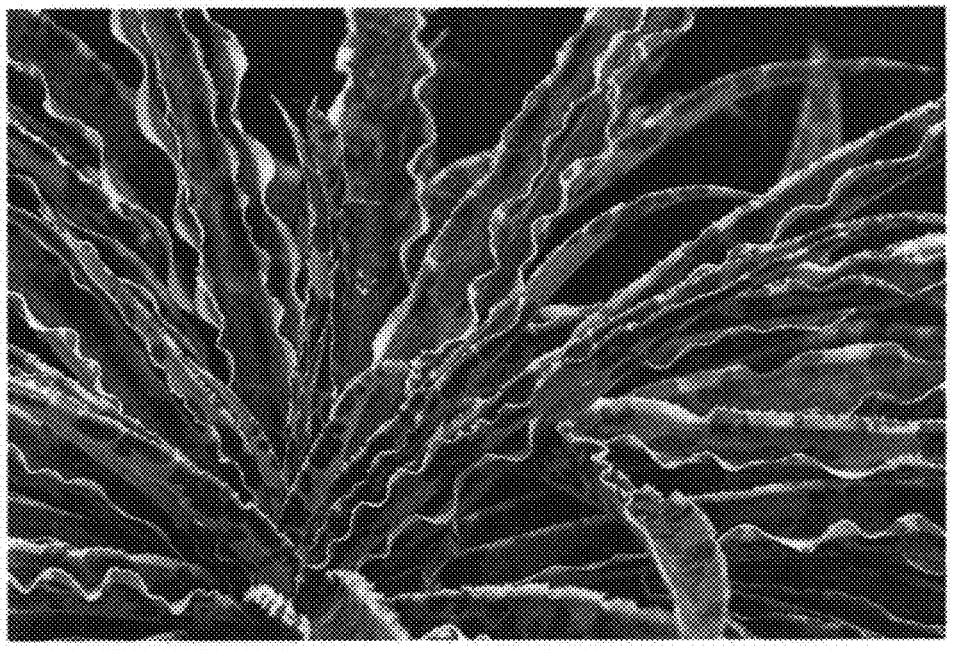
FIG. 2 shows a close-up of the sinuate foliage with white margins and greyed-purple and cherry spotting.
Figure 3:
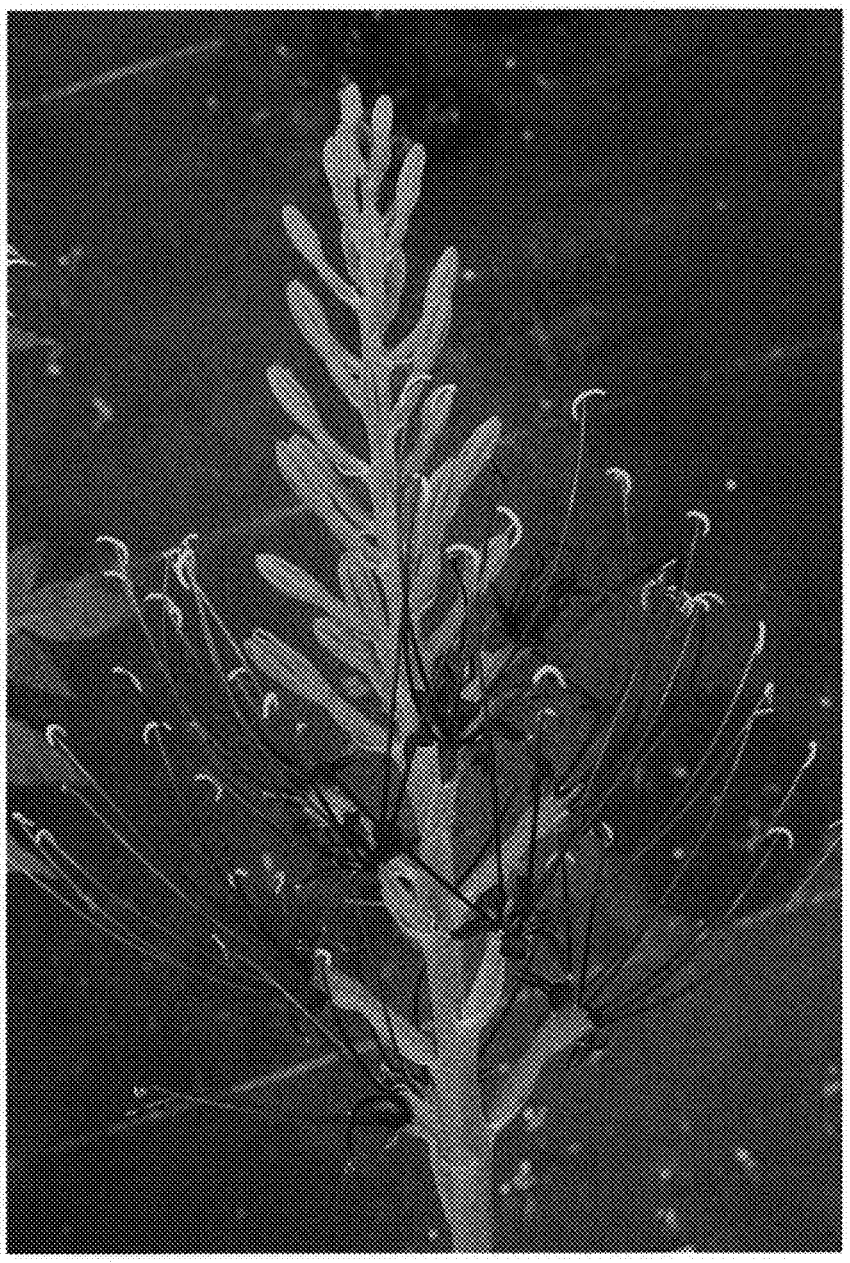
FIG. 3 shows the flower scape with initial flowers and buds.

The following descriptions and color references are based on the 2001 edition of The Royal Horticultural Society Colour Chart except where common dictionary terms are used. The new plant, *Manfreda* 'Cherry Chocolate Chip', has not been observed under all possible environments. The phenotype may vary slightly with different environmental conditions, such as temperature, light, fertility, moisture and maturity levels, but without any change in the genotype. The following observations and size descriptions are of a two-year old plant in a commercial wholesale greenhouse in Zeeland, Mich. with supplemental water and fertilizer as needed.

Botanical classification: *Manfreda undulata* (Klotzsch) Rose;

Variety denomination: 'Cherry Chocolate Chip';

Sport parentage: Uninduced whole-plant sport of *Manfreda* 'Chocolate Chip';

Propagation: Garden division and sterile plant tissue culture;

Time to initiate roots from tissue culture: About 18 days; offsets of 2.5 cm diameter would already have established roots;

Growth rate: Moderate to rapid;

Crop time: About 8 to 10 weeks to finish during the summer in a 3.8 liter container from an established 2.5 cm tissue culture plug;

Rooting habit: Fleshy, lightly branching, with roots up to 15 cm long;

Root color: Variable, nearest RHS NN155B to RHS 158C when active;

Plant shape and habit: Herbaceous monopodial perennial with basal rosettes of leaves emerging from central base, producing a symmetrical flattened mound;

Plant size: Foliage height about 16.0 cm tall from soil line to the top of the leaves and about 60.0 cm wide at the widest point just below soil line;

Foliage description: Lanceolate, simple, fleshy; slightly cupped upward longitudinally, coarsely sinuate; narrowly acute apex; truncate sessile base; margins variegated between 1.5 mm and 4.5 mm wide and irregular spots of between 1.0 mm and 18.0 mm across; spinulose with flexible spinules about 1.0 mm long and 1.0 mm apart;

Leaf size: To about 37.0 cm long, 3.0 cm wide and 2.5 mm thick;

Number of leaves: About 56 per plant;

Foliar fragrance: None observed;

Leaf surface: Glabrous and glaucous adaxial and abaxial;

Leaf blade color: Actively growing.

*Adaxial margin*.—Nearest RHS NN155C with no spots, nearest RHS 62D with spots on lower epidermis and between RHS 61B and RHS 61C in regions with spots on the upper epidermis or both upper and lower epidermis.

*Abaxial margin*.—Nearest RHS NN155C with no spots, nearest RHS 62D with spots on upper epidermis and between RHS 61B and RHS 61C in regions with spots on the lower epidermis or both upper and lower epidermis.

*Adaxial longitudinal center*.—Nearest RHS 137A with spots a blend between RHS N189A and RHS N187A.

*Abaxial longitudinal center*.—Along midrib nearest RHS 138B with spots nearest RHS 137B, toward perimeter nearest RHS 137B with spots nearest RHS 147A.

Leaf blade color: Mature.

*Adaxial margin*.—Nearest RHS NN155A with no spots, nearest RHS 63A with spots on lower epidermis and with spots on upper or both upper and lower epidermis nearest RHS 61A.

*Abaxial margin*.—Nearest RHS NN155A in regions with no spots, and blushed with nearest RHS 61C with spots on upper epidermis and nearest RHS 61A with spots on lower or both lower and upper epidermis.

*Adaxial longitudinal center*.—Between RHS 138A and RHS 138B with spots nearest RHS N187A.

*Abaxial longitudinal center*.—Between RHS 146C and RHS 147C with spots between RHS N187A and RHS 187A.

Spines color: Variable between RHS N155B and RHS N155C;

Petiole: Sessile;

Veins: Absent;

Stem: Short, completely covered with leaves;

Inflorescence: Tall, upright, stiff raceme; flowering portion to about 42.0 cm long and 26.0 cm wide;

Peduncle: Glabrous, glaucous; with about 41 cauline leaves before flowers; about 258.0 cm tall, 1.9 cm diameter at base and 11.0 mm diameter before flowers;

Peduncle color: Nearest RHS N187B with glaucous coating, nearest RHS N187A with green undertone when glaucous coating removed;

Pedicle: Typically sessile;

Flowers: Perfect; actinomorphic, high nectariferous; lasting about three days; about 4.2 cm long from base of ovary to tepal apex, about 14.8 cm long from base of ovary to tip of anther, and about 15.0 cm across from the anther tips;

Flower fragrance: Highly fragrant;

Flower facing: Upwardly;

Tepals: Six; in two identical sets of three; glaucous abaxial; glabrous both adaxial and abaxial; acute apex; basal 15.0 mm fused; distal portion recurved to about 270 degrees; about 3.2 cm long above ovary and 7.0 mm wide above fusion point;

Tepal color: Abaxial below fusion point nearest RHS N138D, above fusion point lighter than RHS N138D with undertone of nearest RHS N186C; adaxial below fusion point base nearest RHS 59A, midsection nearest RHS 144D and distal portion above fusion point nearest RHS 187A;

Androecium: Six; exserted beyond tepals;

*Filaments*.—Glabrous; lustrous; proximal 8.0 mm adnate to corolla base; about 11.6 cm long and 1.0 mm diameter above fusion point; color base nearest RHS 187A developing to nearest RHS 85B distally before anther.

*Anther*.—Glabrous; lanceolate with rounded apices; longitudinal, versatile; about 2.2 cm long, 2.0 mm across and 1.5 mm thick; color nearest RHS N186C.

*Pollen*.—Abundant; color nearest RHS 5B.

Gynoecium: Single; 10.2 cm long;

*Style*.—Exserted; glabrous; lustrous; about 7.4 cm long and 2.0 mm diameter at base; color between RHS N186A and RHS 187A.

*Stigma*.—Turbinate with apex mammillate in tri-parted star; about 2.0 mm long and 2.5 mm across; color base and sides nearest RHS N186A, apical star lighter than RHS 198D.

*Ovary*.—Inferior; ellipsoidal; about 2.6 cm long and 8.0 mm diameter; color nearest RHS N138D.

Bract: Subtending each flower; typically one main bract with two smaller side bracts; each lanceolate, acute apices, truncate base, with entire margin, glaucous, glabrous; main bract to about 20.0 mm long and 10.0 mm across at base;

Bract color: Main bract abaxial RHS N187B with base between RHS 138B and RHS 138C, main bract adaxial nearest RHS 138C; side bracts abaxial and adaxial nearest RHS 193C;

Fruit: Tri-valved loculicidal capsule; ellipsoidal with rounded base and acute apex; about 4.0 cm long and 1.6 cm across; color at maturity blend between RHS 156B and RHS 159C;

Seed: Flattened; dried; shape irregular; about 6.0 mm long and 5.0 mm across; color nearest RHS 202A;

Disease resistance: *Manfreda* 'Cherry Chocolate Chip' has not been observed to be resistant to diseases common to agaves beyond that which is normal for *Manfreda*. The plant is xeromorphic and survives well with minimal water once established. Hardiness at least from USDA zone 7b. Extent of winter hardiness has not been tested.

I claim:

1. A new and distinct cultivar of ornamental *Manfreda* plant named 'Cherry Chocolate Chip' as herein described and illustrated.

* * * * *